United States Patent [19]

Keränen et al.

[11] Patent Number: 5,029,245

[45] Date of Patent: Jul. 2, 1991

[54] PROCEDURE FOR CONTROLLING A RADIATION SOURCE AND CONTROLLABLE RADIATION SOURCE

[75] Inventors: Heimo Keränen; Jouko Malinen, both of Oulu, Finland

[73] Assignee: Valtion Teknillinen Tutkimuskeskus, Vuorimiehentie, Finland

[21] Appl. No.: 457,694

[22] PCT Filed: Jun. 23, 1988

[86] PCT No.: PCT/FI88/00103

§ 371 Date: Jan. 19, 1990

§ 102(e) Date: Jan. 19, 1990

[87] PCT Pub. No.: WO88/10462

PCT Pub. Date: Dec. 29, 1988

[30] Foreign Application Priority Data

Jun. 25, 1987 [FI] Finland ................................. 872824

[51] Int. Cl.⁵ .............................................. G01J 1/32
[52] U.S. Cl. .................................... 250/205; 356/328
[58] Field of Search ................ 250/205; 356/319, 326, 356/328, 420

[56] References Cited

U.S. PATENT DOCUMENTS

| 4,022,531 | 5/1977 | Orazio et al. | |
|---|---|---|---|
| 4,443,695 | 4/1984 | Kitamura | |
| 4,449,821 | 5/1984 | Lee | 356/319 |
| 4,455,562 | 6/1984 | Dolan et al. | |
| 4,566,797 | 1/1986 | Kaffka et al. | 356/420 |
| 4,681,454 | 7/1983 | Breemer | 250/205 |
| 4,790,654 | 12/1988 | Clarke | 356/326 |

FOREIGN PATENT DOCUMENTS 0110201 6/1984 European Pat. Off.
2025090 1/1980 United Kingdom.

Primary Examiner—David C. Nelms
Assistant Examiner—Que T. Le
Attorney, Agent, or Firm—Kane, Dalsimer, Sullivan, Kurucz, Levy, Eisele & Richard

[57] ABSTRACT

The present invention concerns a procedure for controlling a radiation source which has been implemented with the aid of light-emitting diodes, or LEDs, from the radiation produced by them being separated the desired wavelength range, of which the intensity is controlled or maintained constant. The radiation source is implemented by means of a LED row (2) formed of semiconductor chips, or LED elements (21, 22, 23, ..., 26), from the radiation of which is separated a wavelength range ($\Delta\lambda_1$, $\Delta\lambda_2$, ...) depending on the location of the LED element in said arrays with an optical means dispersing the radiation to a spectrum, and the intensity of the radiation in this wavelength range, or of the output radiation, is controlled or maintained constant by observing the intensity thereof and regulating with its aid the current passing through the respective LED element. The wavelength ranges of the output radiation are selected electrically by activating a suitable LED element (21, 22, 23, ..., 26) in the LED row (2).

9 Claims, 5 Drawing Sheets

PROCEDURE FOR CONTROLLING A RADIATION SOURCE AND CONTROLLABLE RADIATION SOURCE

BACKGROUND OF THE INVENTION

1. Field of the Invention

The present invention concerns a procedure for controlling a radiation source, said radiation source being implemented with the aid of light-emitting diodes, or LEDs, of the radiation produced by them the desired wavelength range being separated and the intensity of this radiation range being controlled or kept constant.

The present invention also concerns a controllable radiation source which has been composed of light-emitting diodes, or LEDs, and which comprises optical means for separating the desired wavelength range from the radiation produced by said LEDs and means for controlling the intensity of said wavelength range or keeping it constant.

2. Description of the Prior Art

A radiation source of the kind described is used for instance in spectrometers and photometers. In frequent cases the radiation source is the most significant factor limiting the capacity of performance and usability of an instrument. In apparatus meant to be used in industrial conditions, as radiation source have usually been employed thermal radiators, such as sources based on an incandescent filament, for instance. Their problem is, however, poor optical efficiency and consequent high heat dissipation, as well as poor vibration tolerance, short service life and difficulty of modulation.

In recent years the development of semiconductor technology has introduced on the market efficient lasers based on semiconductor junctions, and light-emitting diodes, or LEDs. They afford several advantages over traditional radiation sources: for instance, small size and low energy consumption, good reliability, long service life (even more than $10^°$ hours), high operating speed, easy connection to optic fibres. Furthermore, they can be electrically modulated with ease. Semiconductor radiation sources are nowadays available for the wavelength range about 400 nm to over 10 $\mu$m; admittedly, though, for operation at room temperature only up to about 3200 nm. The said range is usable in quantitative and qualitative analysis of most substances.

Semiconductor lasers are nearly ideal radiation sources for spectrometers in view of their narrow spectrum. However, high price and poor stability are their problems. It is also a fact that the selection of standard wavelengths is scanty, particularly in the near IR range. LEDs enable, owing to their wider radiation spectrum, a considerably wider wavelength range to be covered, and they are also lower in price. The spectral radiance of LEDs is on the same order as that of most thermic radiation sources, or higher.

The radiations spectrum of LEDs is mostly too wide to allow them to be used as such in spectroscopic measurements. Moreover, the shape of the radiation spectrum, the peak wavelength and the radiant power change powerfully with changing temperature and driving current, and with time.

In spectrometer designs of prior art based on the use of LED sources, the measuring band is separated from the LEDs, usually, with the aid of separate filters, or the LED is used without filtering, in which case the resolution will also be poor. The variation of radiation intensity has most often been compensated for, either by mere electric compensation or by maintaining constant temperature of the LED, which has lead to a demanding and expensive mechanical design. Owing to the high price and difficult manipulation of the filters (e.g. miniaturizing, cutting), the number of wavelength bands in such pieces of apparatus is usually small (2 to 10).

SUMMARY OF THE INVENTION

The object of the present invention is to eliminate, among others, the drawbacks mentioned above and to provide a novel procedure for controlling a radiation source, and a controllable radiation source. This is realized with the aid of the characteristic features of the invention stated in the claims hereto attached.

With the aid of the invention the following advantages are gained, among others. On the basis of the procedure of the invention a controllable radiation source can be realized which is simple as to its construction and contains no moving parts. Furthermore, the radiation source can be realized in a design with small external dimensions. Good wavelength resolution can be achieved in spite of small size. The wavelength resolution is determined, in the first place, by the size of the LED elements (typically only 300 $\mu$m by 300 $\mu$m) and by the angular dispersion and dimensions of the optics which disperse the radiation into a spectrum. The number of measuring channels in the spectrometer in which the procedure of the invention is applied may with ease be increased to be several dozen. The amount of required electronic control and driver apparatus is not necessarily dependent on the number of LEDs. According to the procedure, the intensity of the wavelength bands is also stabilized. The creeping of the spectrum of the LEDs and of the total radiant power will then have no influence on the output intensity of the radiation source. According to the procedure, the wavelengths of the radiation source may be electrically selected. The modulation frequency can be made very high if required (e.g. less than 1 $\mu$s per LED). It is possible in connection with the controllable radiation source of the invention to use for detector a single-channel radiometer, in which advantageously one single detector element is used. The procedure, and the radiation source applying it, can be used in the visible light and IR radiation ranges.

The invention may be applied in the transmitter part of the spectrometer. In certain applications it is also possible to integrate the whole spectrometer to be one single component, which may be hermetically encapsulated. A reliable and stable spectrometer, and one which is usable in field work, is obtained with the aid of such integration.

Significant advantages are gainable with the aid of the procedure of the invention, and of the radiation source employing it, in reflection or transmission measurements on diffuse objects, compared with the multiple detector technique, which has become commonly used in recent years. In multiple element spectrometers the diffuse radiation has to be collected on small-sized detector elements through a narrow entrance slit, whereby high optical collection losses are incurred. In the controllable radiation source of the invention, the optical collection losses can be minimized by using for detector the single-channel radiometer mentioned above, which has a large-sized detector element and, at the same time, also a wide collection angle.

BRIEF DESCRIPTION OF THE DRAWINGS

The invention is described in detail in the following with the aid of the attached drawings, wherein.

DESCRIPTION OF THE PREFERRED EMBODIMENTS

In the procedure of the invention the radiation source is realized with a LED array composed of semiconductor chips, or LED elements, or equivalent. From the radiation of the LED elements a wavelength range depending on the location of the LED element in said array is separated with an optical means dispersing radiation to a spectrum, and the intensity of this wavelength range, or output radiation, is controlled or maintained constant by observing its intensity and with its aid regulating the current passing through the respective LED element. The desired wavelength range may then be selected electrically by activating the respective element in the LED array.

Figure 1:
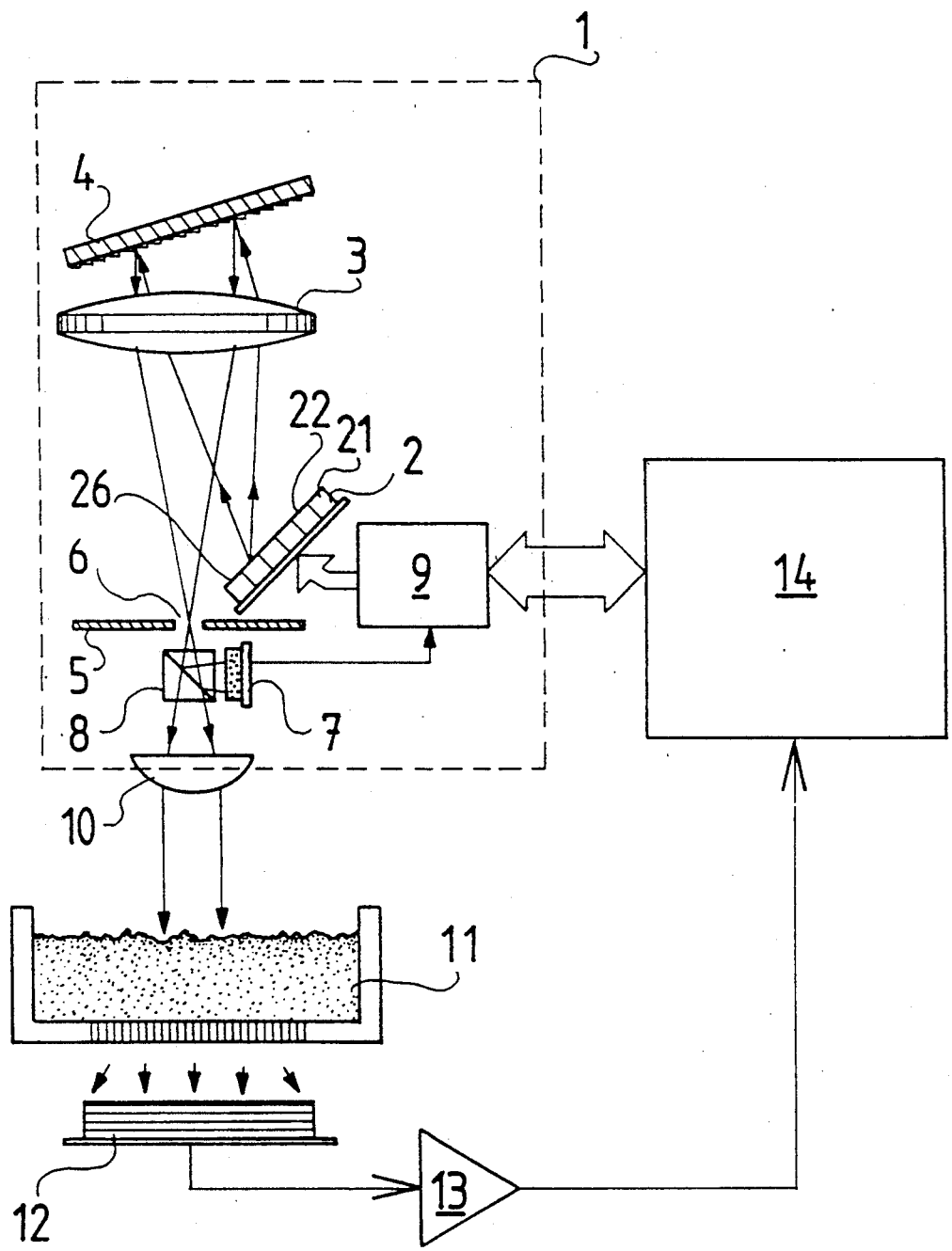
FIG. 1 presents schematically a spectrometer in which the invention is applied.

In the spectrometer of FIG. 1 the procedure of the invention is applied. The radiation source 1 of the spectrometer has been composed of light-emitting diodes, or LEDs. Specifically, the radiation source 1 consists of a row of LEDs 2 which comprises a plurality of side-by-side LED semiconductor chips, or LED elements 21, 22, 23, ..., 26, which are all similar. The radiation source further comprises optical means for separating the desired wavelength range from the radiation produced by the LEDs, and means for maintaining the intensity of the radiation in the wavelength range constant or on desired level. Said optical means consist of optical pieces of equipment, such as lenses, mirrors, gratings, slits and beam dividers, the radiation produced by the LEDs being collected and dispersed to a spectrum with the aid of said means, and the radiation of the desired wavelength range being directed on an output slit or equivalent. The optical means in the spectrometer of FIG. 1 include a radiation-collecting lens 3, a reflection grating 4 dispersing the radiation to a spectrum, and a stop 5 presenting an output slit 6. It is equally possible to use for radiation-collecting component e.g. a concave mirror, and in place of the reflection grating one may use a transmission grating or a prism. These components may also be combined by using, for instance, a focussing reflector or transmission grating.

The controllable radiation source 1 of the invention further comprises optical means and a detector 7 for observing and/or measuring the intensity of the outgoing radiation. The optical means employed in the spectrometer of FIG. 1 consist of a beam divider 8. The radiation source also comprises a driver and control means 9, to which the detector 7 has been connected. The driver and control means 9 is connected to the LED row 2, to each of its elements 21, 22, ..., 26. With the aid of the driver and control means 9, the desired LED element is selected. Thus from the radiation produced by each LED element the desired wavelength range is directed on the output slit, 6 this wavelength range depending on the location of the LED element 21, 22, ..., 26. From the radiation going out from the radiation source, part is separated with the aid of the optical means to go to the detector 7, the current flowing through the respective LED element and producing the radiation in question being regulated in accordance with the intensity data supplied by the detector and in such manner that the radiation intensity of that wavelength range, and thus the intensity of the output radiation, is constant.

Also other optical means may further be attached to the radiation source 1. In FIG. 1, the output radiation passing through the output slit 6 is rendered parallel with a lens 10, whereafter it is directed on the object of measurement, 11. After the object of measurement, in the direction of propagation of the radiation, follows a receiver 12, in which capacity in measurements made on diffuse objects advantageously serves a wide-area radiometer. The electric signal from the receiver 12 is amplified in an amplifier 13 and fed to a calculation unit 14, and it is possibly displayed on a display provided in conjunction therewith. With the calculating unit 14, or by controls on a panel provided in conjunction therewith, the driver and control unit 9 of the radiation source 1 may possibly also be controlled.

For reflection and/or transmission measurements, it is advantageous to devise at least the radiation source 1 to be an integral unit. It can be suitably shielded against ambience, for instance enclosed in a hermetically sealed housing, for improved reliability.

Figure 3:
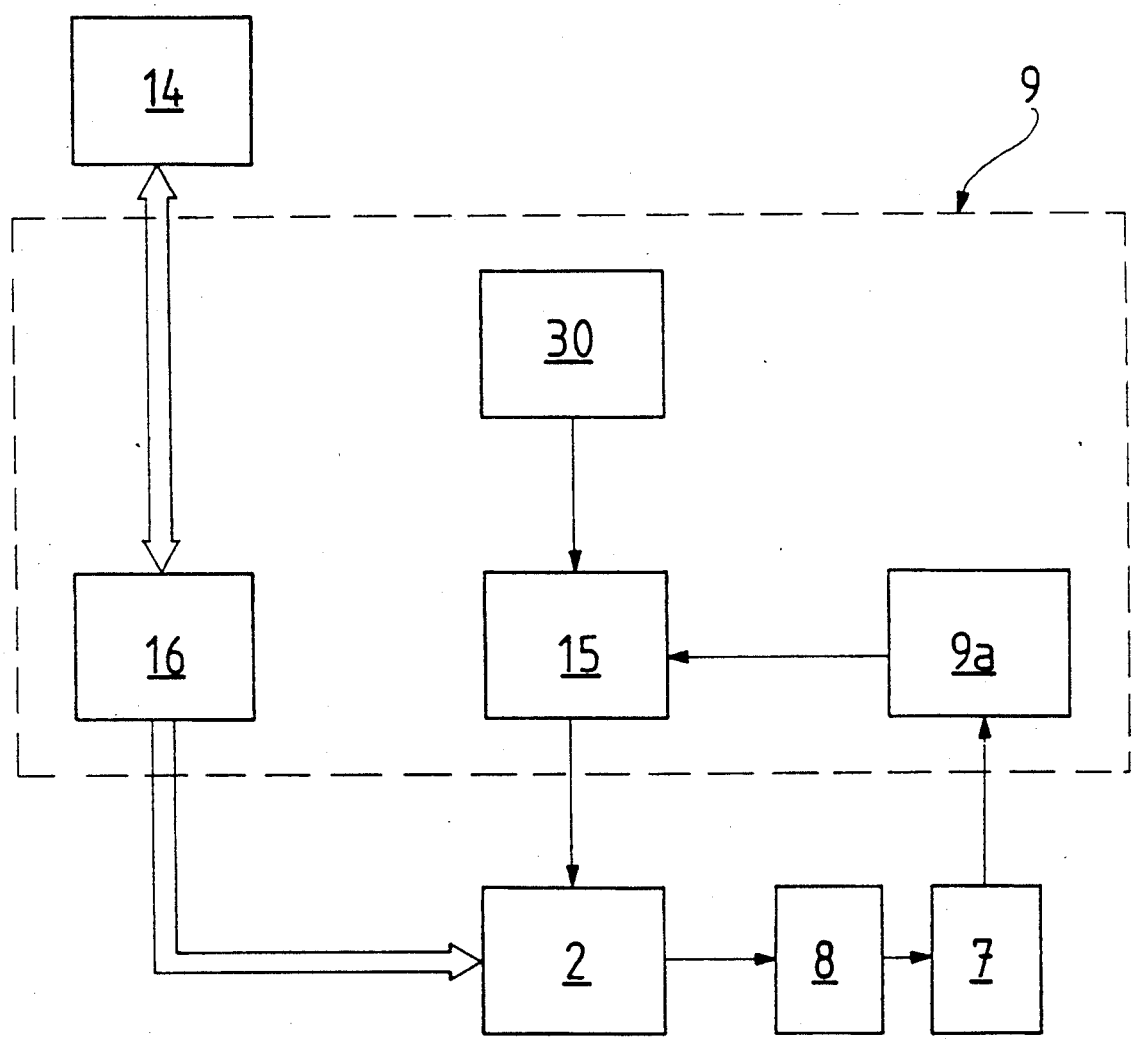
FIG. 3 presents in the form of a block diagram a LED row and its driver and control means.

The circuitry of the driver and control means 9 is presented in block diagram form in FIG. 3. The LED elements 21, 22, ..., 2(N−1), 2N (N=an integer 1, 2, 3, ...) has been connected over a current control circuit 15 to a voltage source 30. The LED elements are connected to a selector means 16, such as a decoder, and this is connected to the calculating unit 14. The desired LED element, for instance the element 23, and the desired wavelength range of the output radiation from the radiation source are selected with the aid of the selector means 16. Part of the radiation obtained from the LED elements is picked up with the aid of the optical means 8 and carried to the detector 7. The detector 7 is connected with the controller 9a. The current control circuit 15 is governed by the controller 9a with the aid of the signal from the detector 7, in such manner that the output signal of the detector has constantly the desired magnitude, whereby the intensity of the output radiation also maintains the desired level.

FIG. 2 illustrates the spectrum of the output radiation obtained by the procedure of the invention. In the rectangular coordinates, the ordinates represent the radiation intensity I and the abscissae, the wavelength. The radiation spectrum of a standard LED has the shape of a broad bell curve, L, FIG. 2A. The spectra of the radiation coming from, a radiation source 1 according to the invention are narrow bands of desired height, or ranges, S, FIGS. 2B–2E, within the range delimited by the bell curve L.

The spectrometer of FIG. 1 and the radiation source therein employed operate in principle as follows. The driver and control means 9 selects and activates in the LED row 2 the first LED element 21. The radiation of the LED element is collected with the lens 3 and sent as a parallel beam to the reflection grating 4. The lens 3 further produces a spectrum of the radiation reflected by the grating on the stop 5. That part of the radiation (wavelength range Δλ₁) passes through the output slit 6 which is determined by the location of the LED element 21 in the row and by the locations and dimensioning of the other optical means 3,4,6. From the lens 10, a parallel output radiation is obtained, striking the object of measurement 11.

Figure 2A:
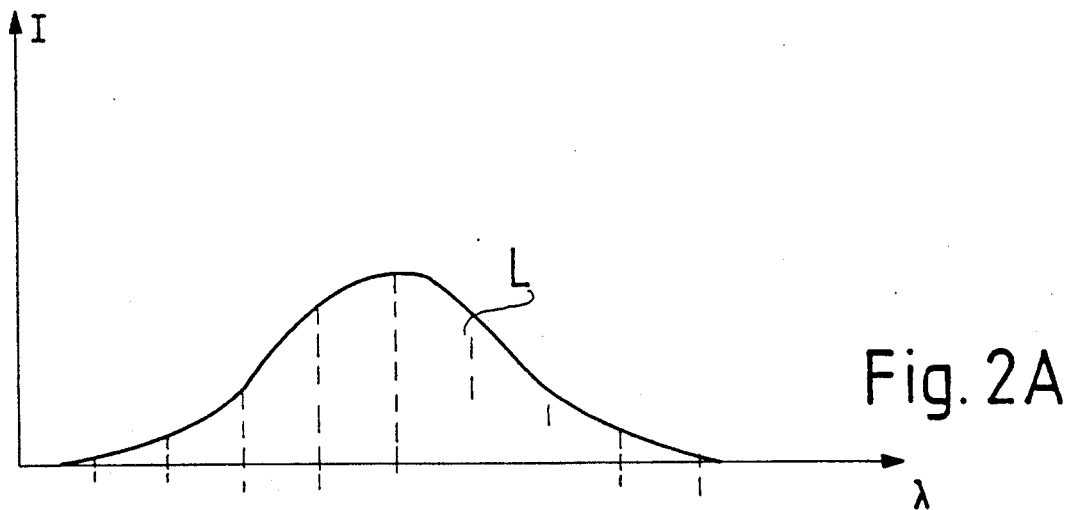
FIG. 2 presents by way of example the radiation spectrum of a LED and the radiation spectrum achievable with the aid of the invention.
Figure 2B:
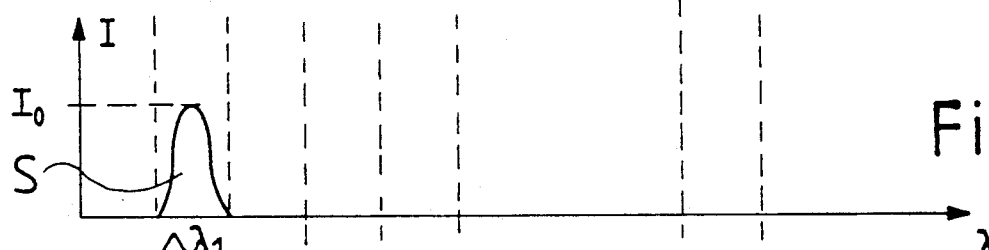
Figure 2C:
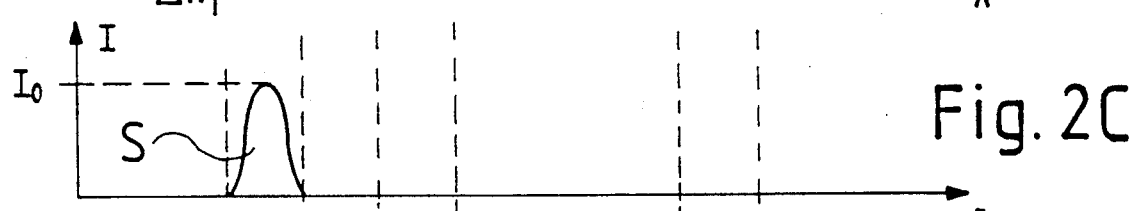
Figure 2D:
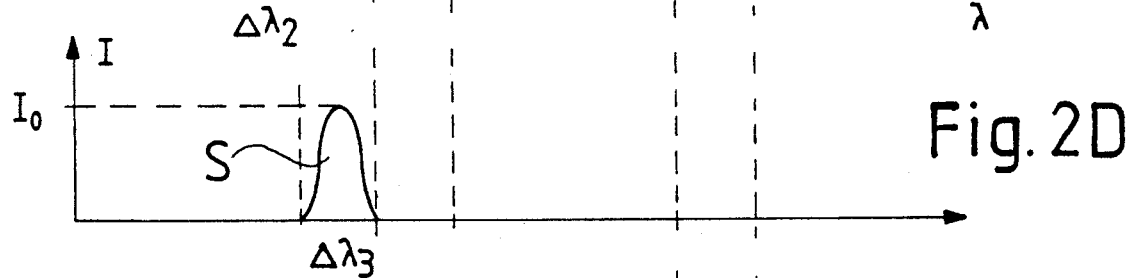
Figure 2E:
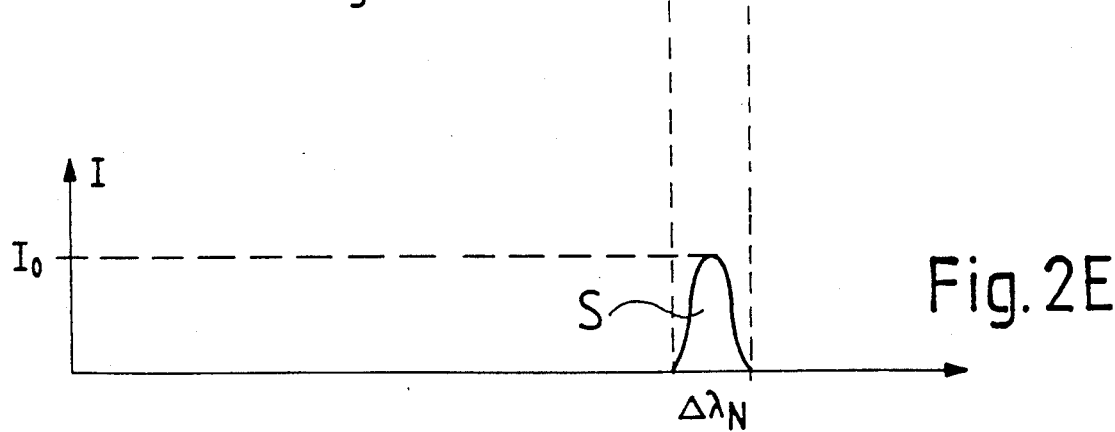

Through the optical means 8, part of the output radiation is directed to strike the detector 7, and the signal representing the intensity that has been obtained is recorded with the driver and control means 9. The driver and control means adjusts the current going to the LED element 21 to have a value such that the signal obtained from the detector 7 rises to desired level, whereby the intensity of the output radiation also assumes the desired value, e.g. $I_o$. Hereafter the actual measurement takes place in the wavelength range $\Delta\lambda_1$ (FIG. 2B) and the result is recorded in the calculating unit 14. Next, the driver and control means 9 activates the LED element 22 and, after the output intensity has similarly been adjusted to required level, measurement takes place in the wavelength range $\Delta\lambda_2$ (FIG. 2C). The driver and control means 9 activates all LED elements 21...2N in succession and measurements are similarly carried out in the wavelength ranges $\Delta\lambda_1, \ldots, \Delta\lambda_N$ (FIG. 2E), whereafter the driver and control means 9 activates again the LED element 21, and so on. The calculating unit 14 is electrically synchronized with the driver and control means 9 so that all results of measurement that have been recorded can be coordinated with the correct wavelength ranges $\Delta\lambda_1, \ldots \Delta\lambda_N$.

Figure 4:
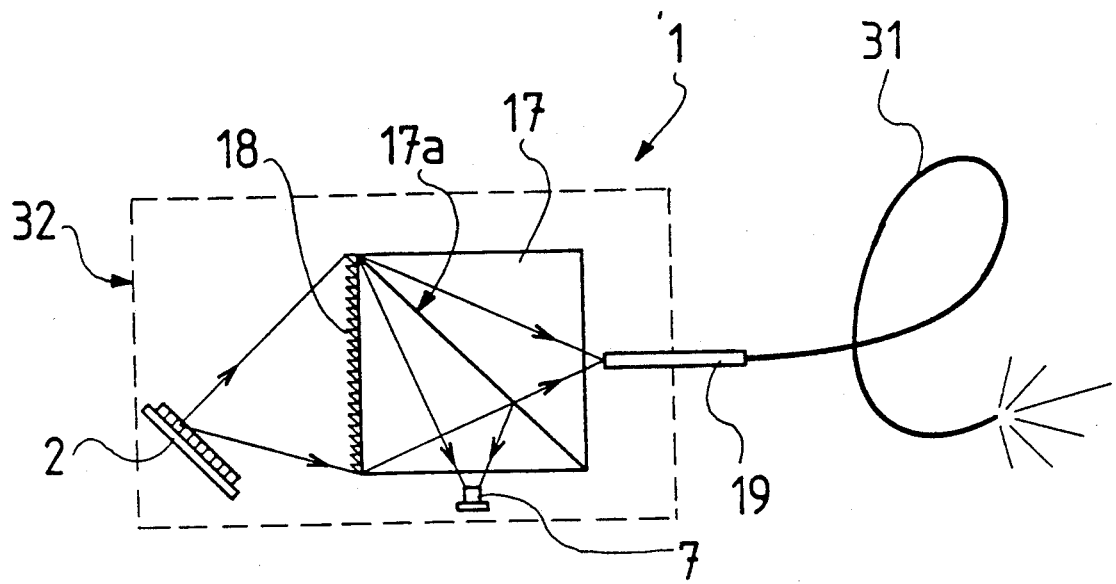
FIG. 4 presents a radiation source according to the invention in which an optic fibre is utilized.

In the foregoing in the spectrometer of FIG. 1 the optical means for collecting the radiation from the LED rows, for dispersing it to a spectrum and for directing the desired wavelength range on the output slit 6, comprising a lens 3 and a reflection grating 4 or equivalent. In the radiation source of FIG. 4, said optical means comprise a beam divider cube 17 and on the surface thereof a focussing transmission grating 18. In this case the detector 7 for monitoring the intensity of the output radiation has been disposed in conjunction with the beam divider cube 17. The dividing interface 17a of the beam divider cube reflects to the detector 7 part of the radiation going through the beam divider cube to the output slit. In the capacity of output slit serves an optic fibre connector 19 to which an optic fibre 31 has been connected. The radiation source 1 with its LED row 2 is enclosed in a suitable housing 32.

Figure 5:
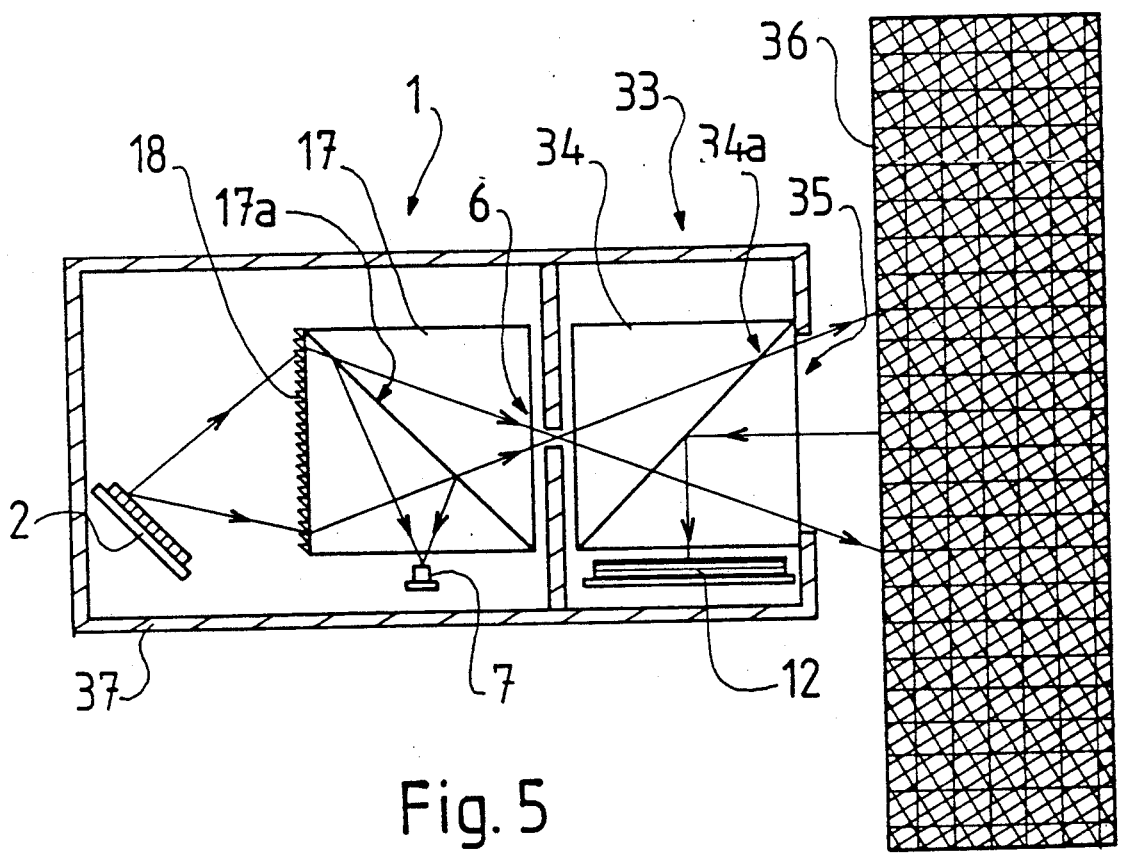
FIG. 5 presents schematically a reflection spectrometer in which the invention is applied.

FIG. 5 depicts a compact spectrometer intended for reflection measurements and comprising both the transmitter of the radiation source and the receiver. The radiation source 1 is equivalent in its design with the radiation source of FIG. 4, and the same reference numerals are employed to indicate equivalent components. In front of the the radiation source 1, in the direction of propagation of the radiation, a receiver 33 has been disposed. This receiver consists of a beam divider 34 and a receiver detector 12. The output radiation is carried put from the device through an aperture 35. The object of measurement 36, which is a reflecting surface, is placed in front of the radiation beam coming from the spectrometer. The radiation reflected from the object of measurement 36 returns through the aperture 35 to the beam divider 34 of the receiver 33, from the dividing interface 34a of which the major part of the radiation is reflected to the receiver detector 12 and is detected. Both the radiation source 1 and the receiver 33 have in this case been integrated to constitute a single unit, which may be provided with a hermetically sealed housing 36 if required. In this way the reflection spectrometer can be made into a device usable in the field. The radiation from the spectrometer can be directed to strike the object of measurement 36 without any separate output optics, as has been set forth in the foregoing, or by using e.g. a standard lens optic system or a fibre-optic component.

Figure 6A:
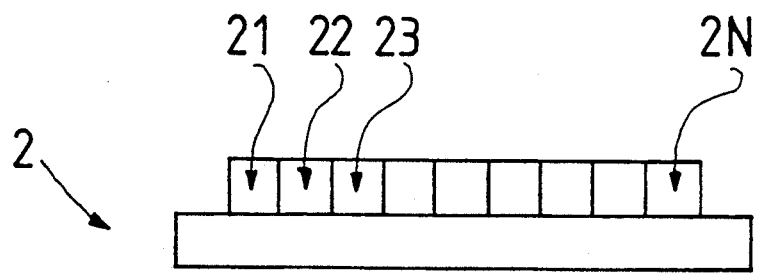
FIG. 6 presents a radiation source row, FIG. 6B, by which a LED row, FIG. 6A, may be replaced.
Figure 6B:
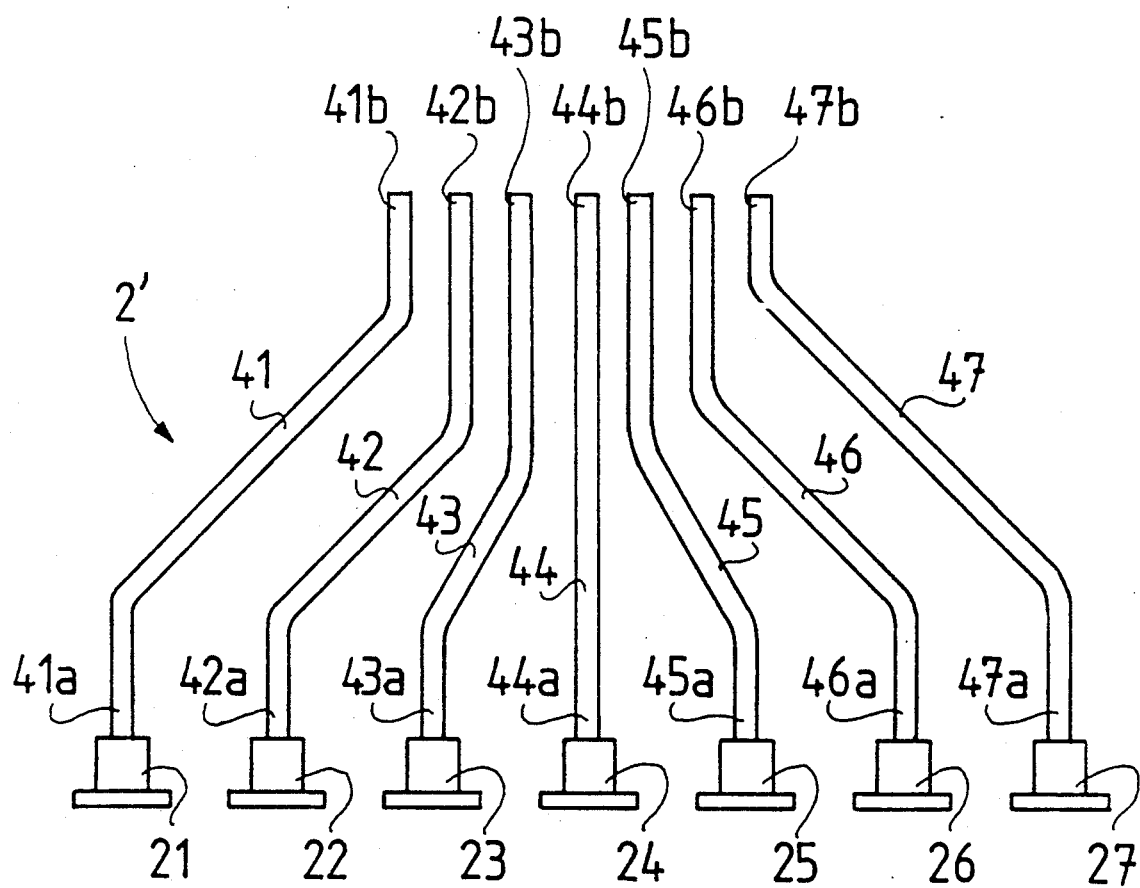

The LED row may be replaced with another type of radiation source row, as can be seen in FIG. 6. FIG. 6A presents, seen from the side, a LED row 2 comprising consecutively placed LED elements 21, 22, ..., 2N. The alternative radiation source row depicted in FIG. 6B comprises a number of LED elements or separate, encapsulated LEDs 21, 22, ..., 27, to each of them connected an optic fibre 41, 42, ..., 47 by its first end 41a, 42a, ..., 47a. The other ends 41b, 42b, ..., 47b of the optic fibres are arranged in a configuration such as is desired. The ends of the optic fibres are then close together and are thus equivalent e.g. to the LED row presented in the foregoing.

It should be noted that although the invention has been presented in the foregoing in the first place only with the aid of one measuring apparatus, it is obvious that the procedure for controlling a radiation source, and the controlled radiation source, can be employed in numerous other applications as well in which a stable, or easy to control, radiation source is needed which produces radiation within a given wavelength range in a plurality of alternatingly active, and if need be narrow, wavelength bands. Moreover, in the embodiment examples of the invention presented in the foregoing a LED row or equivalent is employed, but it is also possible to use in its stead a LED matrix or any other equivalent LED array.

We claim:

1. A procedure for controlling a radiation source, said radiation source being implemented with light-emitting diodes (LEDs), wherein a desired wavelength range of the radiation produced by said LEDs may be separated, and wherein said desired wavelength range may have an intensity controlled or maintained constant by regulating currents passing through said LEDs, said currents causing said LEDs to produce radiation, characterized in that the radiation source is implemented by means of a LED array formed of LED elements, from the radiation of which is separated a wavelength range depending on the location of the LED element in said array with an optical means dispersing the radiation into a spectrum, and the intensity ($I_o$) of the radiation in this wavelength range is controlled or maintained constant by observing the intensity thereof and regulating with its aid the current passing through the respective LED element, said wavelength range being selected electrically by activating one of said LED elements of said LED array.

2. A controllable radiation source which is composed of light-emitting diodes (LEDs), and which comprises optical means for separating a desired wavelength range having an intensity from the radiation produced by the LEDs, said radiation being produced by passing a current through said LEDs, and means for controlling the intensity of said desired wavelength range, characterized in that the radiation source comprises a LED array which comprises a plurality of LED elements;

The optical means comprises optical apparatus, with the aid of said apparatus the radiation produced by the LEDs may be collected and the radiation may be dispersed into a spectrum and the desired wavelength range of the spectrum may be directed on an output slit;

said radiation source further comprises additional optical means and a detector for monitoring and measuring the intensity ($I_o$) of the output radiation; and said radiation source further comprises a driver and control means by the aid of which from the radiation produced by each LED element is selected to the output slit the desired wavelength range, which depends on the location of the LED element in the LED array and from which output radiation part is with the aid of said additional optical means separated to go to a detector according to the intensity values from which the driver and control means regulates the current passing through the respective LED element so that the intensity ($I_o$) of the radiation in said wavelength range and of the output radiation is maintained at desired height.

3. Means according to claim 2, characterized in that the LED elements (21, 22, 23, ..., 26) of the LED array (2,2') are connected together and connected with a current control circuit (15) and a selector means (16) with the aid of which the desired LED element (e.g. 23) and the desired wavelength range ($\Delta\lambda_3$) of the output radiation of the radiation source are selected and which current control circuit (15) is governed by a controller (9a) with the aid of the signal from the detector (7) in such manner that the intensity ($I_o$) of the output radiation continuously maintains the same height.

4. Means according to claim 2 or 3, characterized in that said optical means for collecting and dispersing to a spectrum the radiation produced by the LEDs and for directing the desired wavelength range on the output slit (6) comprise a focussing reflection or transmission grating.

5. Means according to claim 2 or 3, characterized in that said optical means for collecting and dispersing to a spectrum the radiation produced by the LEDs and for directing the desired wavelength range on the output slit (6) and on the detector (7) comprise a beam divider cube (17) and on then surface thereof a transmission grating (18).

6. Means according to claim 5, characterized in that the detector (7) for observing the intensity of the output radiation has been disposed in conjunction with the beam divider cube (17) so that the beam divider cube also serves as an optical means associated with the detector.

7. Means according to any one of the preceding claims 2-6 for performing reflection and/or transmission measurement, characterized in that at least the radiation source (1) has been formed to be an integral unit (32).

8. Means according to any one of the preceding claims 2-6 for performing reflection measurements, characterized in that the radiation source (1) and the receiver (33) have been integrated to constitute an integrated unit, which is advantageously provided with a hermetically sealed housing (37).

9. Means according to any one of the preceding claims 2-6, characterized in that the LED array (2) consists of a plurality of LED elements or separate encapsulated LEDs (21, 22, ..., 27, FIG. 6B) to each of which is connected an optic fibre (41, 42, ..., 47) by its first end (41a, 42a, ..., 47a) and the second ends (41b, 42b, ..., 47b) have been arranged in a desired configuration.

* * * * *